US 6,684,129 B2

(12) United States Patent
Salisbury, Jr. et al.

(10) Patent No.: US 6,684,129 B2
(45) Date of Patent: *Jan. 27, 2004

(54) MASTER HAVING REDUNDANT DEGREES OF FREEDOM

(75) Inventors: J. Kenneth Salisbury, Jr., Mountain View, CA (US); Akhil J. Madhani, Glendale, CA (US); Gary S. Guthart, Mountain View, CA (US); Gunter D. Niemeyer, Mountain View, CA (US); Eugene F. Duval, Menlo Park, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/121,283

(22) Filed: Apr. 11, 2002

(65) Prior Publication Data

US 2003/0023346 A1 Jan. 30, 2003

Related U.S. Application Data

(63) Continuation of application No. 09/398,507, filed on Sep. 17, 1999, and a continuation-in-part of application No. 09/508,871, filed as application No. PCT/US98/19508 on Sep. 18, 1998.
(60) Provisional application No. 60/116,844, filed on Jan. 22, 1999, and provisional application No. 60/059,395, filed on Sep. 19, 1997.

(51) Int. Cl.[7] .............................................. G06F 19/00

(52) U.S. Cl. ...................... 700/245; 700/131; 700/132; 700/258; 600/101; 600/102; 600/109; 600/118; 600/426; 600/429; 600/595; 606/1; 606/130; 128/897; 128/923; 340/3.5

(58) Field of Search ................................. 700/245, 131, 700/132, 258; 606/1, 130; 600/102, 426, 429, 595, 101, 118, 109; 128/897, 923; 340/3.5

(56) References Cited

U.S. PATENT DOCUMENTS 3,923,166 A * 12/1975 Fletcher et al. ................ 414/4

(List continued on next page.)

FOREIGN PATENT DOCUMENTS

| WO | WO 95/01757 | 1/1995 |
| WO | WO 99/50721 | 10/1999 |

OTHER PUBLICATIONS

Lai et al., Evaluating control modes for constrained robotic surgery, 2000, IEEE, pp. 603–609.*

(List continued on next page.)

Primary Examiner—William A. Cuchlinski, Jr.
Assistant Examiner—McDieunel Marc
(74) Attorney, Agent, or Firm—Townsend and Townsend and Crew LLP; Mark D. Barrish, Esq.

(57) ABSTRACT

An input device for robotic surgical techniques and other applications has a handle supported by a linkage with a redundant degree of freedom, the joints being movable with at least one more degree of freedom than the handle. At least one joint of the linkage is actively driven to prevent the linkage from approaching singularities of the joint system, motion limits of the joints, and also to drive the linkage toward a freely articulatable configuration. A robotic master controller can include an arm assembly supporting a gimbal having a redundant linkage, with the arm primarily positioning the gimbal in a three dimensional controller workspace and the gimbal coupling the arm to the handle with four rotational degrees of freedom. One or more additional degrees of freedom may also be provided for actuation of the handle, to close the jaws of a surgical grasper.

18 Claims, 12 Drawing Sheets

U.S. PATENT DOCUMENTS

| | | | |
|---|---|---|---|
| 4,942,538 A | | 7/1990 | Yuan et al. |
| 5,078,140 A | | 1/1992 | Kwoh |
| 5,182,641 A | | 1/1993 | Diner et al. |
| 5,184,601 A | | 2/1993 | Putman |
| 5,217,003 A | | 6/1993 | Wilk |
| 5,222,499 A | | 6/1993 | Allen et al. |
| 5,279,309 A | | 1/1994 | Taylor et al. |
| 5,305,203 A | | 4/1994 | Raab |
| 5,368,015 A | | 11/1994 | Wilk |
| 5,382,885 A | * | 1/1995 | Salcudean et al. ..... 318/568.11 |
| 5,402,801 A | | 4/1995 | Taylor |
| 5,417,210 A | | 5/1995 | Funda et al. |
| 5,458,574 A | | 10/1995 | Machold et al. |
| 5,499,320 A | | 3/1996 | Backes et al. |
| 5,572,999 A | | 11/1996 | Funda et al. |
| 5,625,576 A | | 4/1997 | Massie et al. |
| 5,631,973 A | | 5/1997 | Green |
| 5,649,956 A | | 7/1997 | Jensen et al. |
| 5,695,500 A | | 12/1997 | Taylor et al. |
| 5,697,939 A | | 12/1997 | Kubota et al. |
| 5,737,500 A | | 4/1998 | Seraji et al. |
| 5,738,649 A | | 4/1998 | Macoviak |
| 5,748,767 A | | 5/1998 | Raab |
| 5,762,458 A | | 6/1998 | Wang et al. |
| 5,791,908 A | | 8/1998 | Gillio |
| 5,792,135 A | | 8/1998 | Madhani et al. |
| 5,808,665 A | | 9/1998 | Green |
| 5,855,583 A | | 1/1999 | Wang et al. |
| 5,876,325 A | | 3/1999 | Mizuno et al. |
| 5,931,832 A | | 8/1999 | Jensen |
| 5,971,976 A | * | 10/1999 | Wang et al. .................... 606/1 |
| 2002/0120363 A1 | * | 8/2002 | Salisbury et al. ........... 700/254 |

OTHER PUBLICATIONS

Cleary et al., State of the art surgical robotics clinical applications and technology challenges, 2001, Internet, pp. 1–26.*

Howe et al., Robotics for surgery, 1999, Internet, pp. 211–242.*

Fisch et al., Chapter 4: Haptic devices for virtual reality, telepresesce and human–assistive robotics, no date, pp. 4–1–4–24.*

Towsend and Townsend and Crew, Copy of the allowed claims of 09/398,507, 2003, pp. 1–4.*

Marck, Minimally invasive and robotic surgery, 2001, Internet, pp. 568–567.*

Hayashibe et al., Laser–pointing endoscope system for intra––operative 3D geometric registration, 2001, Internet/IEEE, pp. 1543–1548.*

Baker et al., "On the inverse kinematics of redundant manipulators" The International Journal of Robotics Research (1988) 7(2):3–21.

Caccavale et al. "Experiments of kinematic control on a redundant robot manipulator with non–spherical wrist" Laboratory Robotics and Automation (1996) 8:25–36.

Kosuge et al., "Unified approach for teleoperation of virtual and real environment—manipulation based on reference dynamics" IEEE International Conference on Robotics and Automation (1995) pp 938–943.

Kosuge et al., "Unifiedd approach for teleoperation of virtual and real environment for skill based teleoperation" IEEE International Conference on Robotics and Automation (1994) pp 1242–1247.

Kyong–Sok et al., "Manipulator control at kinematic singularities: A dynamically consistent strategy" IEEE International Conference on Robotics and Automation (1995) pp. 84–88.

Madhani, Akhil J., "Design of Teleoperated Surgical Instruments for Minimally Invasive Surgery" Ph.D. Dissertation, Massachusetts Institute of Technology, Department of Mechanical Engineering (Feb. 1998), pp. 1–251.

Wampler, "Wrist singularities: Theory and practice" Khatib et al. Eds., The Robotics Review 2, MIT Press (1992) 173–189.

Wampler, "Inverse kinematic functions for redundant spherical wrists" IEEE Transactions on Robotics and Automation (1989) 5(1):106–111.

Wampler, "An implementation of inverse kinematic functions for control of a redundant wrist" IEEE International Conference on Robotics and Automation (1989) pp. 914–919.

Wampler, "The inverse function approach to kinematic control of redundant " Maerican Control Conference (1988)pp. 1364–1369.

* cited by examiner

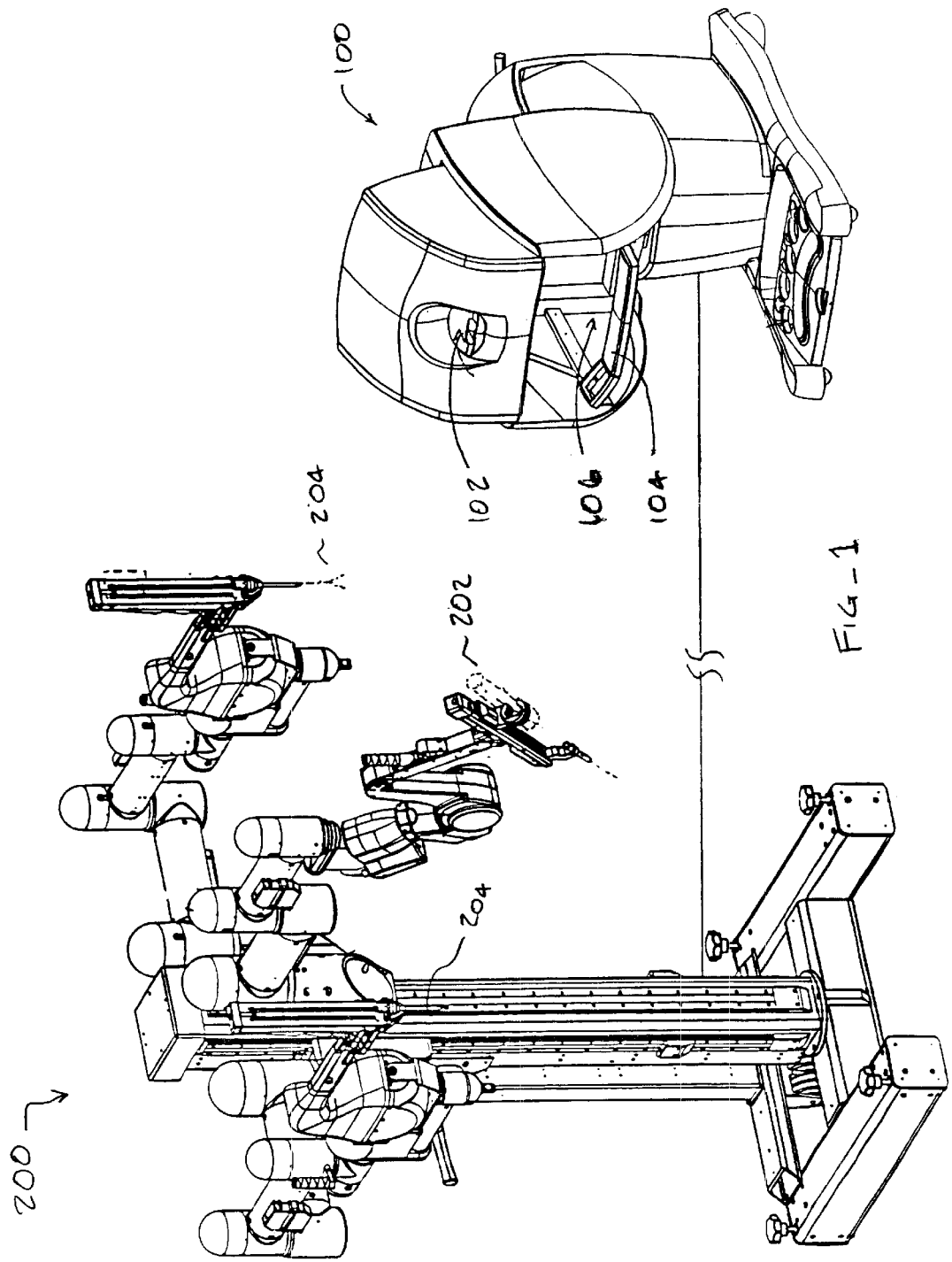

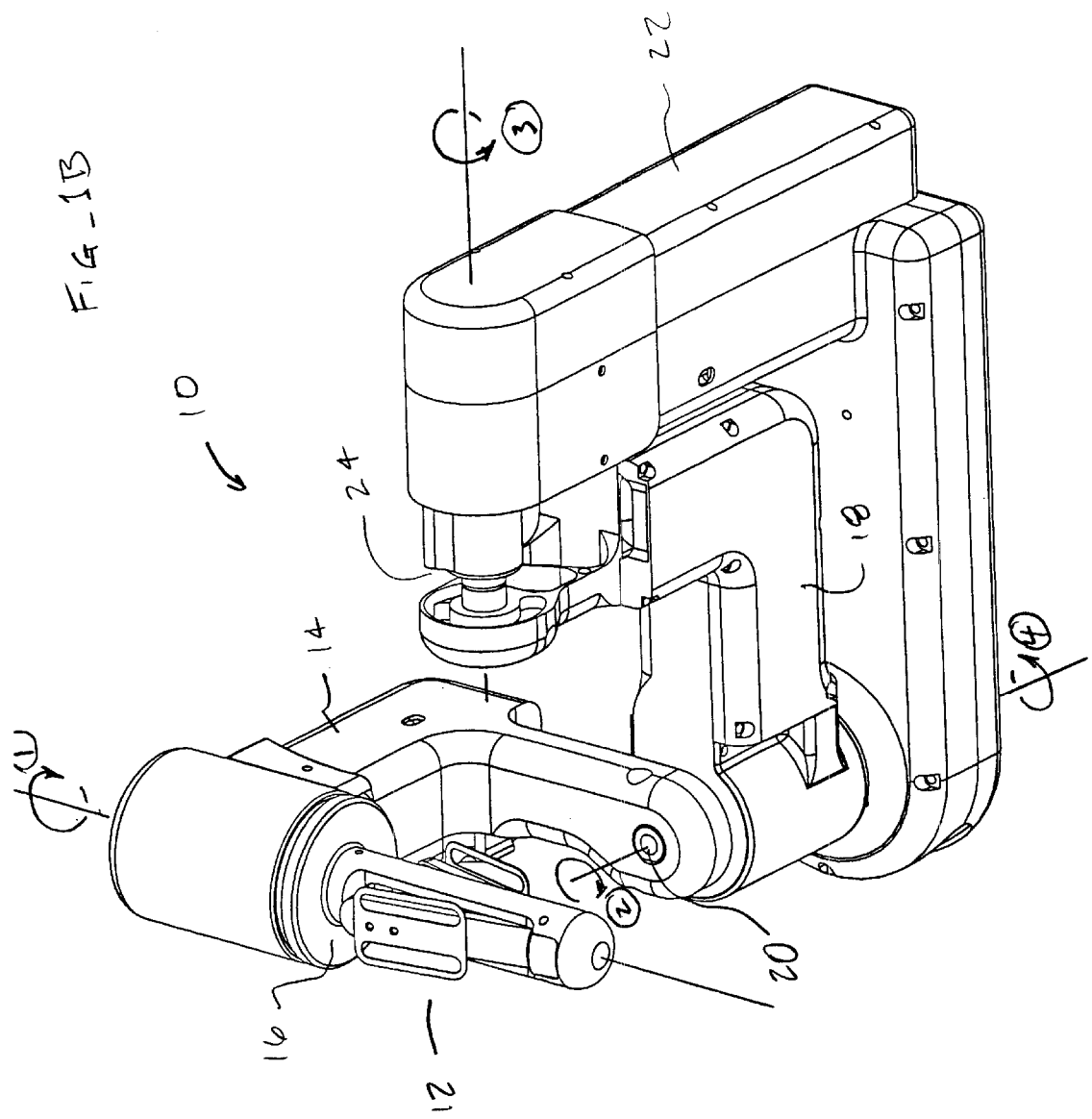

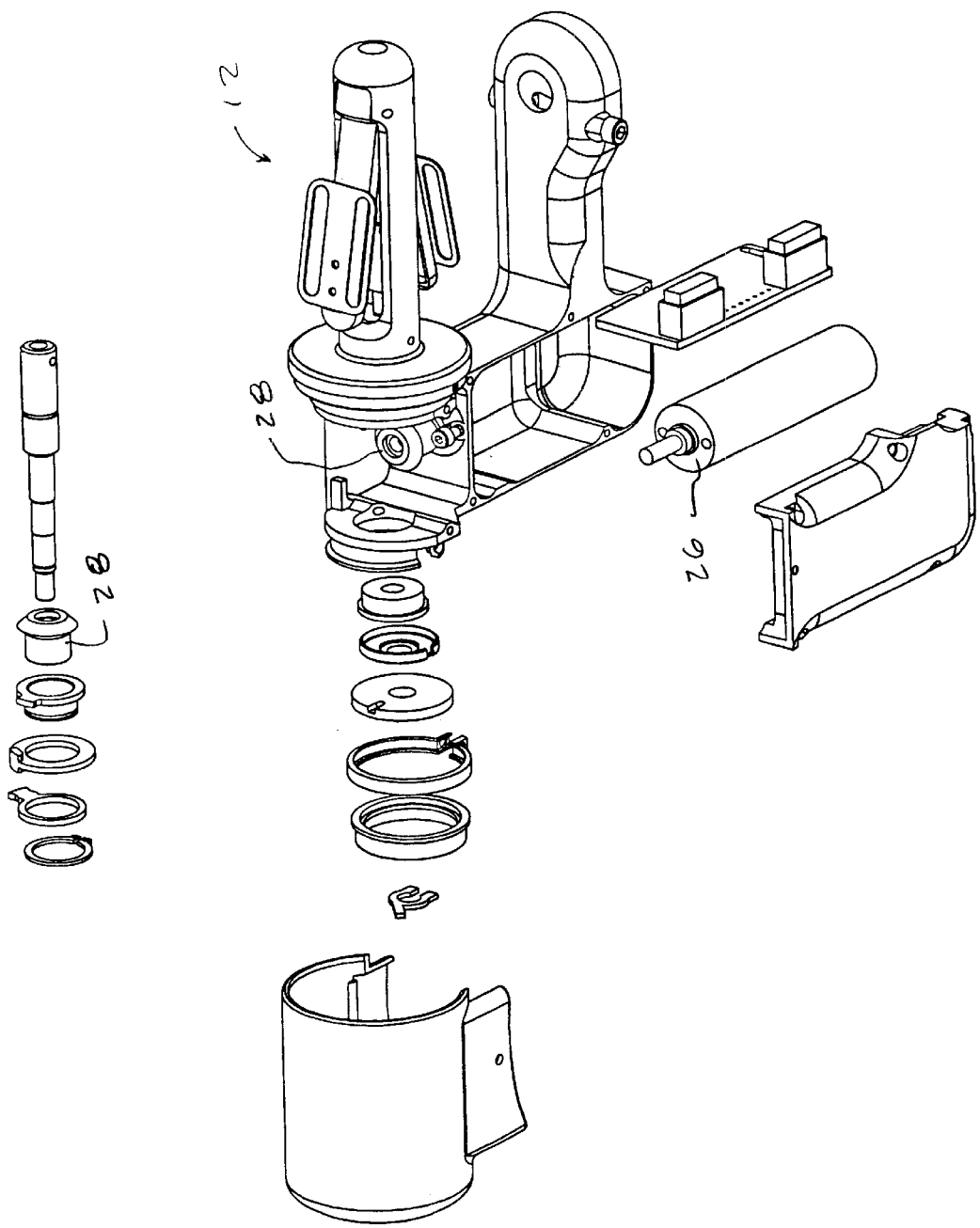

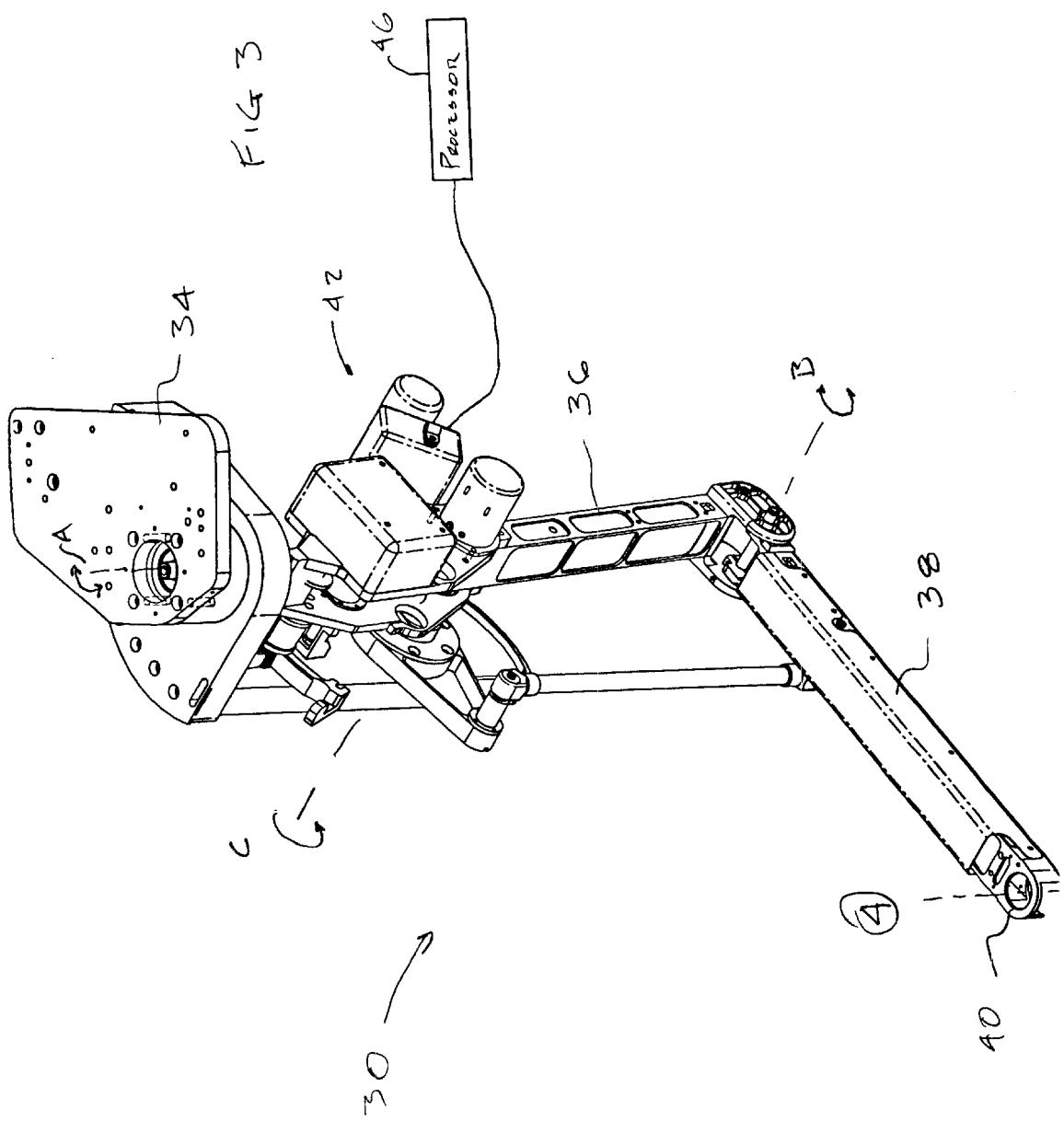

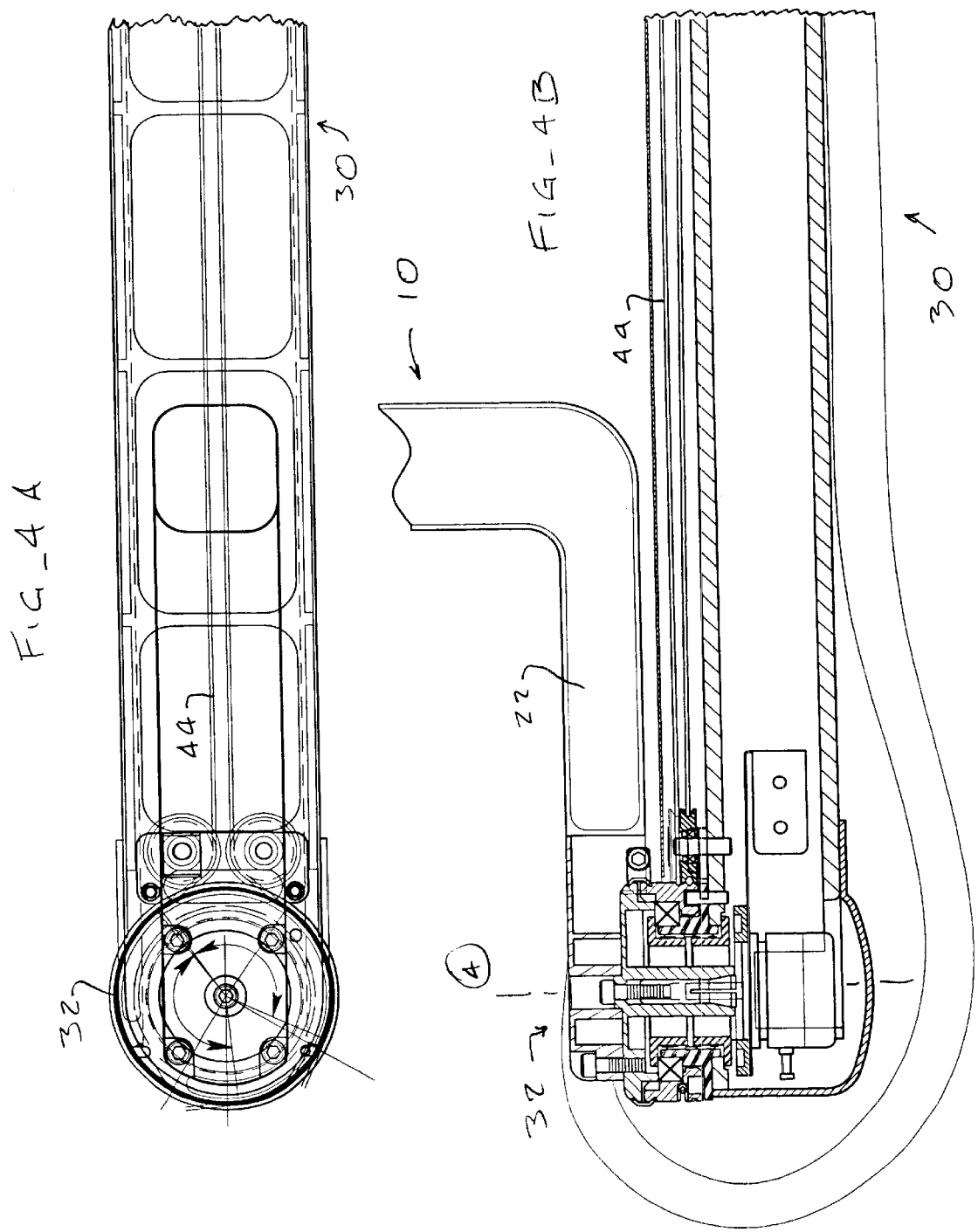

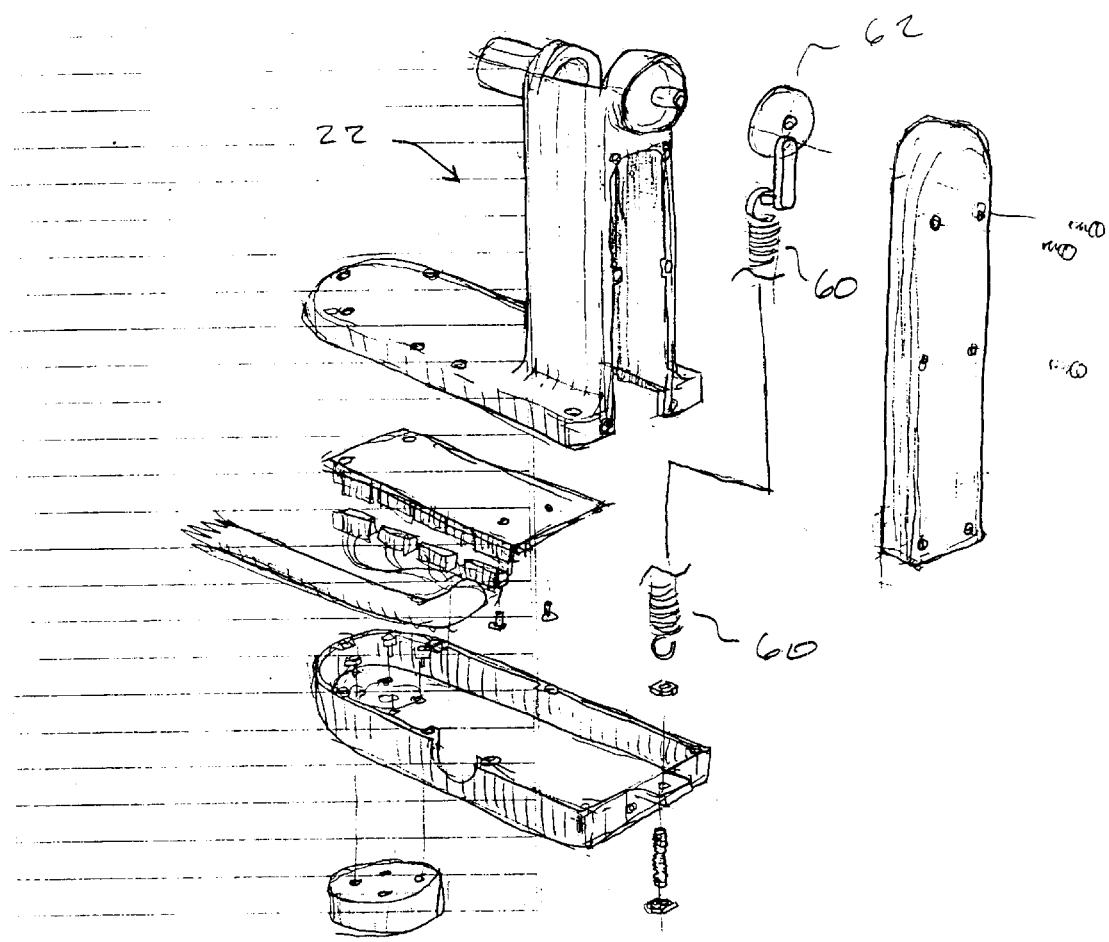
FIG_7

MASTER HAVING REDUNDANT DEGREES OF FREEDOM

CROSS-REFERENCES TO RELATED APPLICATIONS

The present application is a continuation of U.S. patent application Ser. No. 09/398,507 filed on Sep. 17, 1999, which is a non-provisional patent application of and claims the benefit of priority from U.S. Provisional Patent Application No. 60/116,844 filed Jan. 22, 1999; and is also a continuation-in-part of U.S. patent application Ser. No. 09/508,871 filed on Jul. 17, 2000, which was a 371 of PCT Application No. US98/19508 filed on Sep. 18, 1998 (PCT Publication No WO 99/50721), which claims the benefit of priority from U.S. Provisional Patent Application No. 60/059,395 filed on Sep. 19, 1997, the full disclosures of which are incorporated herein by reference.

BACKGROUND OF THE INVENTION

This invention relates to data input devices, and more particularly, provides a master controller which may be used for directing movements of a robot and which is particularly useful for robotically enhanced surgery.

In robotically assisted surgery, the surgeon typically operates a master controller to remotely control the motion of surgical instruments at the surgical site. The controller may be separated from the patient by a significant distance (e.g., across the operating room, in a different room, or in a completely different building than the patient). Alternatively, a controller may be positioned quite near the patient in the operating room. Regardless, the controller will typically include one or more hand input devices such as a joystick, exo-skeletol gloves, or the like. These hand input devices are coupled by a servo mechanism to the surgical instrument. More specifically, servo motors move a manipulator or "slave" supporting the surgical instrument based on the surgeon's manipulation of the hand input devices. During an operation, the controller may employ, via the robotic surgery system, a variety of surgical instruments such as tissue graspers, needle drivers, electrosurgical cautery probes, etc. Each of these structures perform functions for the surgeon, for example, holding or driving a needle, grasping a blood vessel, or dissecting, cauterizing, or coagulating tissue.

To deliver the full potential of this promising new form of surgery, the robotic system will preferably allow movement of the end-effector in both position and orientation. Directing such robotic input is much easier when the surgeon is able to move the hand input device with motions that correspond to the desired motions of the end-effector. Hence, it would be desirable to provide hand input devices which can move in three-dimensional space, and which can also change in orientation about three axes. While a variety of robotic input devices have been proposed, including known force reflecting input devices, exo-skeletal input devices, and the like, these proposed devices have generally had shortcomings, particularly when the system operator desires to manipulate an input device to direct a wide range of end-effector motions such as those that can be imparted when a surgeon's hand manipulates a surgical tool, repositions her hand on the handle of the tool, or the like.

Unfortunately, mechanical linkage systems of known hand input devices do not provide unlimited freedom of movement. In fact, linkage systems for both the slave and the master controller will typically have "singularities". These singularities are linkage configurations in which motion of the linkage is inhibited in at least one direction. Singularities can occur, for example, when two of the pivotal or other axes of motion of the linkage system become aligned, so that they no longer independently contribute to the mobility of the mechanism. Such binding or loss of motion capability of the master and/or slave linkage systems is disadvantageous during robotically assisted surgery.

In minimally invasive robotic surgery procedures, the surgical end effectors will typically be introduced through a small incision or opening into an internal surgical site. To position and orient the end-effector in the internal surgical site, the end-effectors will often be supported at the end of elongate shafts, with one or more joints disposed between the shaft and the end effector. Hence, the linkage systems supporting the end effector may be quite different that the linkage supporting the hand input device of the master controller. Additionally, the surgical end effectors which access the internal surgical site through an opening will often be removed and replaced during surgery. For example, needle graspers may be replaced by a scalpel. It would generally be desirable to avoid and/or decrease loss of mobility due to master singularities and the like, regardless of the specific end effector in use.

In light of the above, it would be desirable to provide improved input devices, robotic surgical apparatus, and robotic methods.

SUMMARY OF THE INVENTION

The present invention provides an input device and method which is particularly useful for robotically-enhanced surgical techniques. The robotic input device (often called a master controller) has a handle supported by a linkage so that the handle can move in space, ideally so that the handle can turn in any orientation. The linkage includes a redundant degree of freedom. At least one joint of the linkage may be actively driven by a processor of the robotic system to prevent the linkage from approaching singularities. In the exemplary embodiment, the master includes an arm assembly which is used primarily to position the handle in the controller workspace. The arm provides three degrees of freedom, and is coupled to the handle by a wrist system having four degrees of freedom. One or more additional degrees of freedom may also be provided for actuation of the handle, for example, to close the jaws of a surgical grasper. Hence, the master may have a total of eight or more degrees of freedom (including end effector actuation).

Work in connection with the present invention has shown that it is not always possible and/or desirable that the master and slave have singularities that correspond. If a robotic surgical system uses a master and slave which are kinematically dissimilar, it is unlikely that the singularities of the master will occur at the same position as those of the slave. Hence, the total number of singularities affecting the system includes those of both the master and those of the slave, as the singularities of the master may prohibit otherwise possible slave motions. The redundant degree of freedom of the master controller described herein can provide a usable workspace with fewer (or even no) singularities to reduce these limits on the system's movement.

BRIEF DESCRIPTION OF THE DRAWINGS

FIG. 1 is a perspective view of a master control workstation and a manipulator system for robotically moving a plurality of minimally invasive surgical instruments.

FIG. 1B is a perspective view of the gimbal used in the input device of FIG. 1A.

FIG. 2 is an exploded view of a link of the gimbal of FIG. 1B.

FIG. 3 is a perspective view of the arm used in the input device of FIG. 1A.

FIGS. 4A and B illustrate the driven joint coupling the gimbal to the arm in the input device of FIG. 1A.

FIG. 7 is an exploded view of another link of the gimbal of FIG. 1B.

DESCRIPTION OF THE SPECIFIC EMBODIMENTS

This application is related to the following patents and patent applications, the full disclosures of which are incorporated herein by reference: PCT International Application No. PCT/US98/19508, entitled Robotic Apparatus, filed on Sep. 18, 1998; U.S. Provisional Patent Application No. 60/111,713, entitled Surgical Robotic Tools, Data Architecture, and Use, filed on Dec. 8, 1998; U.S. Provisional Patent Application No. 60/111,710, entitled Master Having Redundant Degrees of Freedom, filed on Dec. 8, 1998; U.S. patent application Ser. No. 9/287,858, entitled Alignment of Master and Slave in a Minimally Invasive Surgical Apparatus, filed Apr. 7, 1999 (issued as U.S. Pat. No. 6,364,888 on April 2. 2002), and U.S. patent application Ser. No. 09/399,457 entitled Cooperative Minimally Invasive Telesurgical System, filed Sep. 17, 1999.

Figure 1A:
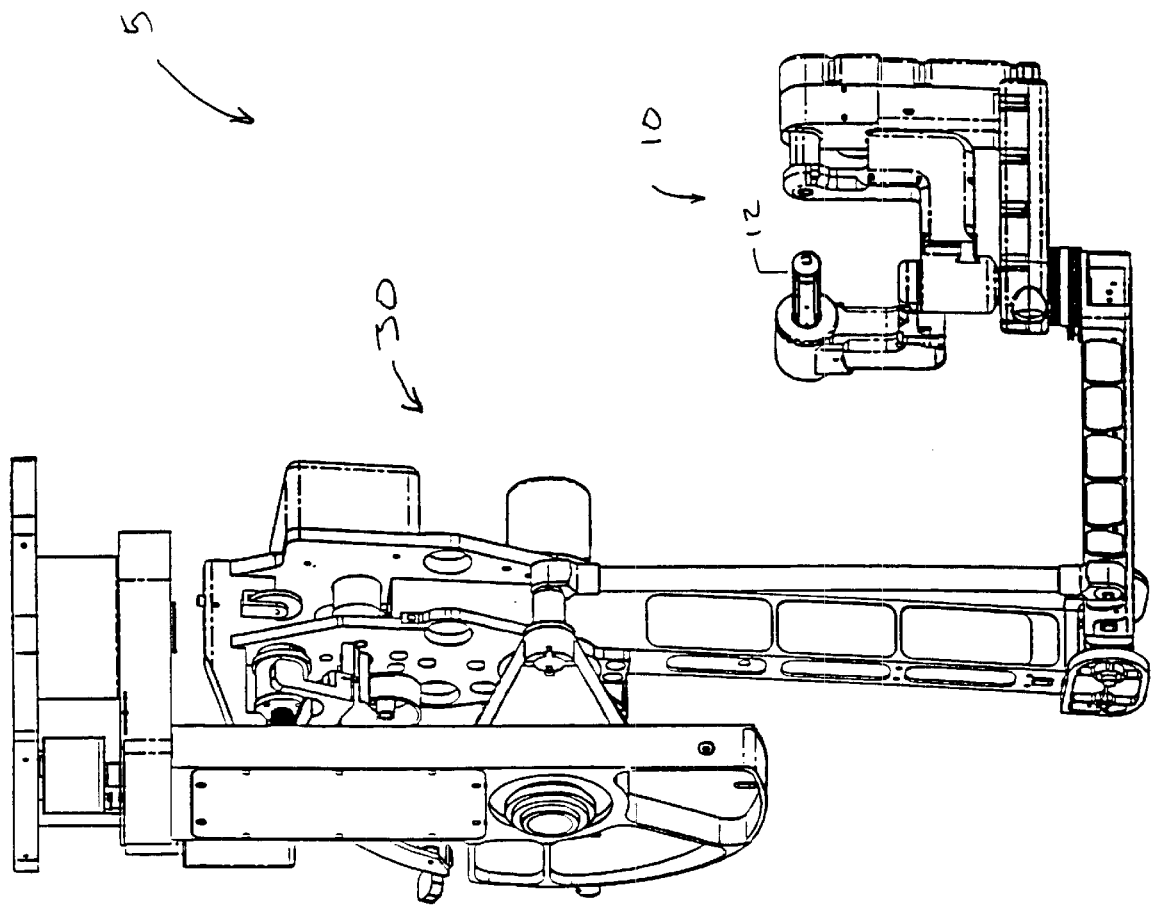
FIG. 1A is a perspective view of a master control input device for use in the workstation of FIG. 1 including a gimbal having a linkage with a redundant orientational degree of freedom and an arm movably supporting the gimbal in a workspace of the control workstation.

Referring to FIG. 1 of the drawings, a master control workstation or surgeon's console of a minimally invasive telesurgical system is generally indicated by reference numeral 100. The workstation 100 includes a viewer 102 where an image of a surgical site is displayed in use. A support 104 is provided on which an operator, typically a surgeon, can rest his or her forearms while gripping two master controls (shown in FIG. 1A), one in each hand. The master controls are positioned in a workspace 106 disposed inwardly beyond the support 104. When using the workstation 100, the surgeon typically sits in a chair in front of the workstation, positions his or her eyes in front of the viewer 102 and grips the master controls one in each hand while resting his or her forearms on the support 204.

FIG. 1 also shows a cart or surgical manipulator system 200 of the telesurgical. In use, the cart is positioned close to a patient for surgery and is then normally caused to remain stationary until the surgical procedure has been completed. Manipulator system 200 typically includes three robotic arm assemblies. One of the robotic arm assemblies is arranged to hold an image capturing device, e.g., an endoscope 202, or the like, which is coupled to display 102 of the workstation. Each of the two other arm assemblies includes a surgical tool 204 having a surgical end effector for treating tissue.

The robotic arms will move and articulate the surgical tools in response to the motions of the input devices at the workstation, so that the surgeon can direct surgical procedures at internal surgical sites through minimally invasive surgical apertures. The workstation 200 is typically used within an operating room with the cart, but can be positioned remote from the cart, even miles away. The exemplary controller workstation and manipulator system for use with the master controller of the present invention is more fully described in co-pending U.S. patent application Ser. No. 09/373,678, entitled Camera Referenced Control in a Minimally Invasive Surgical Apparatus, filed Aug. 13, 1999 (issued as U.S. Pat. No. 6,424,885 on July 23, 2002), the full disclosure of which is incorporated herein by reference. Referring now to FIG. 1A, each master control input device 5 will generally allow movement of a handle 12 within workspace 106 with a plurality of degrees of freedom, typically with six degrees of freedom, three rotational degrees of freedom and three translational degrees of freedom. In the exemplary embodiment, a gimbal or wrist 10 provides primarily rotational degrees of freedom, while an am 30 provides translational degrees of freedom. It should be noted that at least some of these degrees of freedom may be coupled.

Referring now to FIG. 1B, a four-degree of freedom gimbal or wrist 10 allows rotation of actuatable handle 12 about three axes, axis 1, axis 2, and axis 3. More specifically, handle 12 is coupled to a first elbow-shaped link 14 by a first pivotal joint 16. First link 14 is coupled to a second elbow-shaped link 18 by a second pivotal joint 20. Second link 18 is pivotally coupled to a third elbow-shaped link 22 by a third pivotal joint 24. Handle 12 may include a grip actuation sensor such as a Hall effect device. Finger loops may be attached to the handle to avoid slipping.

Referring now to FIG. 2, showing an exploded view of components contained within first link 14, a motor 26 is coupled to handle 12 by beveled gears 28. To sense an angular position of handle 12 about first axis 1, an encoder and/or a potentiometer are coupled to motor 26. Similar motors, potentiometers, and encoders are also provided within each of linkages 18 and 22.

Referring now to FIGS. 1B, 3, 4A, and 4B, wrist 10 is mounted to an articulated arm 30 by a fourth pivotal joint 32 so that the third link moves relative to the arm about fourth axis 4. Arm 30 generally comprises a base mounting plate 34 coupled to an upper arm link 36 and a forearm link 38 by an arm joint system defining arm axes A, B and C. This arrangement generally allows a platform of 40 at the distal end of forearm link 38 to be positioned in a three-dimensional workspace of the controller station. A drive and sensor system is mounted to upper arm link 36 adjacent base 34. The drive and sensor system 42 includes motors coupled to the joints of the arm to articulate the arm about the joints, and encoders and/or potentiometers to sense angular positions of the joints.

As can be understood with reference to FIGS. 1A, 3, 4A, and 4B, motor system 42 includes a motor which drivingly engages link 22 of wrist 10 about a fourth joint 32 via cables 44. Fourth joint 32 is actively driven by these cables, based (at least in part) on input from the joint configuration sensors coupled to first, second, and/or third joints 16, 20, 24. More specifically, angle signals from the sensors are transmitted to a processor 46, which directs drive and sensing system 42 to rotate third link 22 relative to platform 40. As described below, drive system 42 can be used to avoid singularities of the linkage of input device 50. Singularities may be described analytically as the linkage configurations in which a Jacobian matrix defined by the loses rank.

Figure 5A:
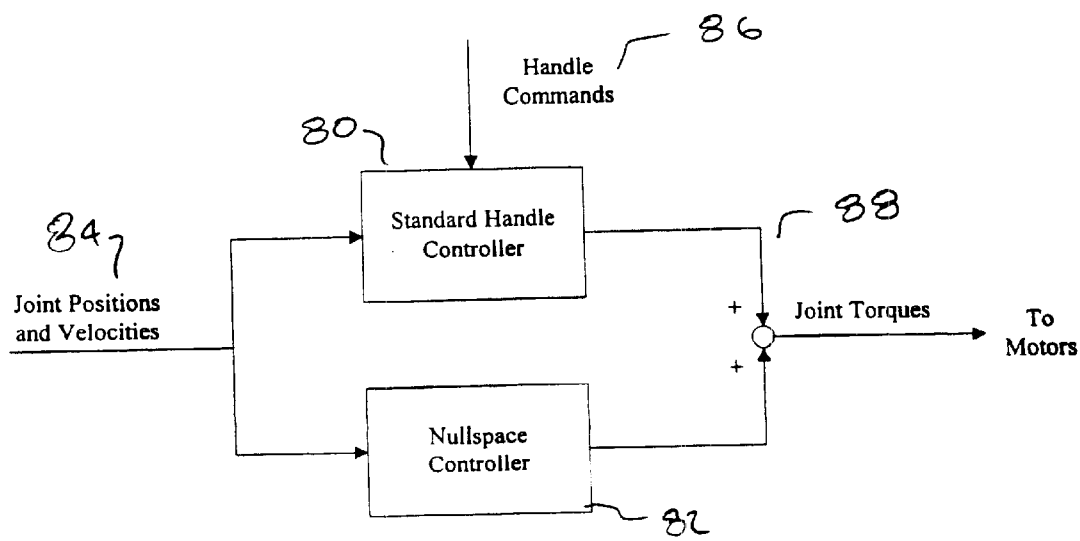
FIGS. 5A and B are block diagrams illustrating a control system for actuating the driven joint of the input device.

FIGS. 5A and B are diagrams schematically illustrating an exemplary method and computer program for driving a master with one or more redundant degrees of freedom, for example, to drive joint 32 so as to avoid singularities of the linkage of wrist 10. A controller 80 accepts handle commands 86, for example, from a force reflecting bilateral master/slave controller so as to provide an indication of forces imposed on the surgical end effector, to reposition the handle into a position corresponding with the end effector as shown in the surgeon's display, to compensate for gravity or friction of the master linkage, and/or the like. Controller 80 also reads the current joint positions and velocities 84 for the master (for example, from the joint position sensors of wrist 10), and from these inputs, computes joint torques 88 to effect handle commands 86. A wide variety of structures might be used as controller 80, including a Cartesian proportional-integral-derivative (P.I.D.) controller, a Cartesian proportional-derivative (P.D.) controller, or the like.

In parallel to controller 80, a second controller 82, sometimes referred to herein as a nullspace controller, also reads the joint positions and velocities from the master so as to compute joint torques to be applied by the motors of master input device 5. The joint torques from both controllers are summed and transmitted or commanded to the drive system 26, 42 of the master. Note that both controllers may transmit torques to one, some, or all driven joints of the master, and that the torques for each motor may simply be added as appropriate. While this parallel controller arrangement is shown in the context of a redundant degree-of-freedom master in a master/slave system, it may also find applications in any redundant degree-of-freedom mechanism to improve performance and address a variety of different goals encoded in a cost function, as described below.

In general, second controller 82 is configured to make use of the redundant degree of freedom of the master linkage system to achieve one or more goals. Examples of such goals are to keep each joint of the wrist at or near a nominal "center" angular position, to drive the linkage system away from singularities, and to generally keep the wrist on the front (preferred) side. It will often be advantageous, for example, to drive one or more joints of the system so as to maintain the axes of the orientational joints with a substantially orthogonal arrangement, or as close to orthogonal as possible for a given handle position in the workspace, within the mechanical and operational constraints of the master system. By driving, for example, joint 32 about axis 4, axes 1–3 may be held closer to an orthogonal yaw-pitch-roll arrangement, thereby minimizing inertia and friction of the master linkage when the handle is rotated in any orientation. In addition to avoiding one or more singularities of the linkage, it may be possible to drive the joint to avoid a joint articulation or range of motion limitation, a workspace limitation, and/or interference with a hand grasping the handle.

More specifically, suitable goals for nullspace controller 82 may (in broad terms) include the following categories:

1) Drive the master linkage away from singularities.
2) Keep the linkage in a preferred configuration.
3) Provide the largest possible range of motion available to the system operator.
4) Provide the best "feel" to the operator—in other words, accomplish 1), 2), and/or 3) without disturbing or distracting the operator.

These objectives are mathematically encoded in the form of a cost function C(q). The cost function calculates and/or assigns a "cost" value for every possible combination of joint positions. The controller uses this cost, generally by attempting to drive the driven joint or joints so as to minimize the calculated cost value. Hence, the cost function, although arbitrary, is derived so that driving the master in a direction which minimizes the cost function will further or achieve the goals described above. It should be understood that an equivalent system may attempt to maximize a "benefit" function, rather than reducing a cost function.

The cost function C(q) may be any smooth function. In the exemplary embodiment, a simple quadratic function can be used to describe and further the above goals. The exemplary cost function is of the form:

$$C(q) = \sum_i w_i(q_i - c_i)^2$$

Wherein i represents each of joints 16, 20, 24, and optionally, 32 (and in some embodiments, one or more positional joints such as the joints of arm 30 at axes A, B, and/or C); $q_i$ is the current location of the joint as indicated by the sensor system of the wrist; while $c_i$ denotes a preferred nominal position of the joint. This preferred position is sometimes referred to herein as the center location or "sweet spot", and may be close to the center of angular movement of the joint. Nonetheless, preferred locations $c_i$ may be biased somewhat away from the actual centers of travel of the joints, for example, to maximize clearance from the surgeon's hand when grasping handle 12. By placing $c_i$ away from undesired locations such as singularities and joint travel limits, and near desired locations such as preferred locations, we can adjust the master behavior.

In the cost function formula, the difference between the current location of each joint and its preferred center location is squared, and the squared value is then adjusted by a weight factor w for that joint. The weight factor may enhanced for joints having a smaller range of motion, for example. The summation of these weighted quantities is generally minimized by driving the wrist about platform 40, as described herein above. This minimization, however, will preferably occur in such a manner so as to avoid disruption of the surgeon's input via handle 12.

Figure 6A:
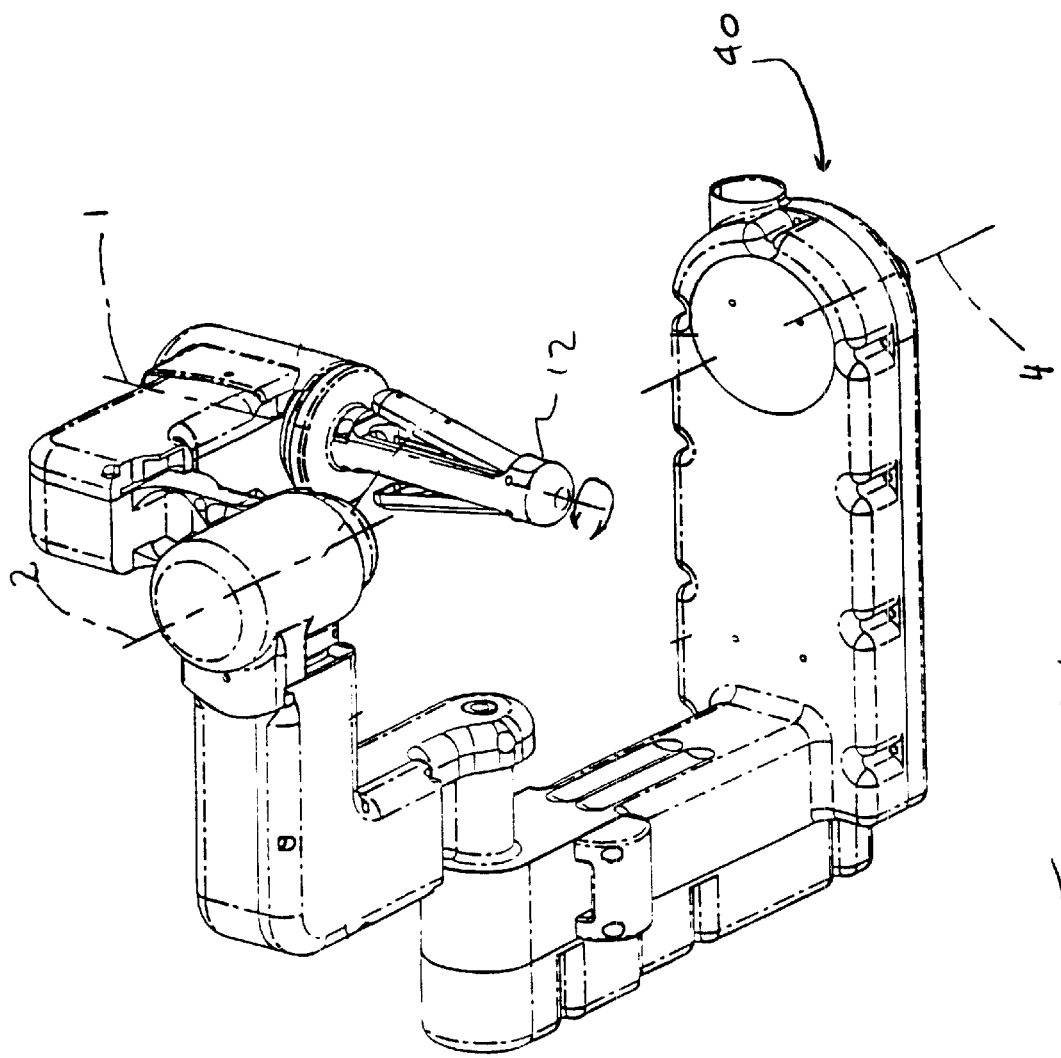
FIGS. 6A–C illustrate alternative configurations of the redundant linkage for a single handle position in the workspace.
Figure 6B:
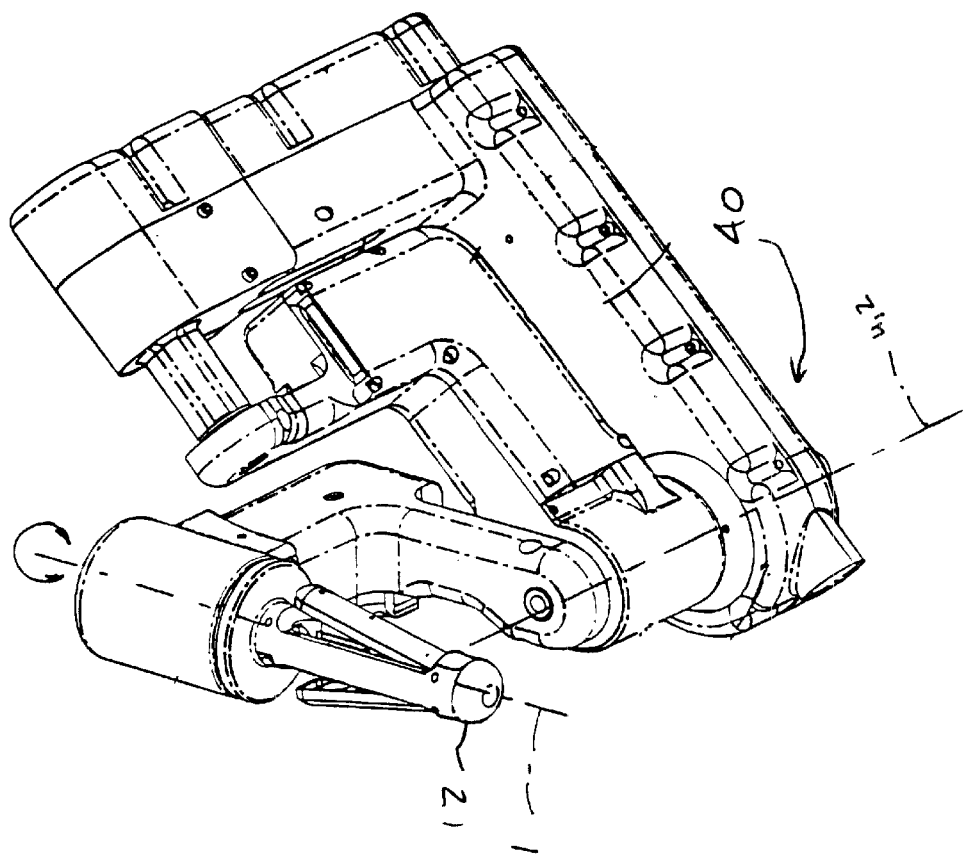
Figure 6C:
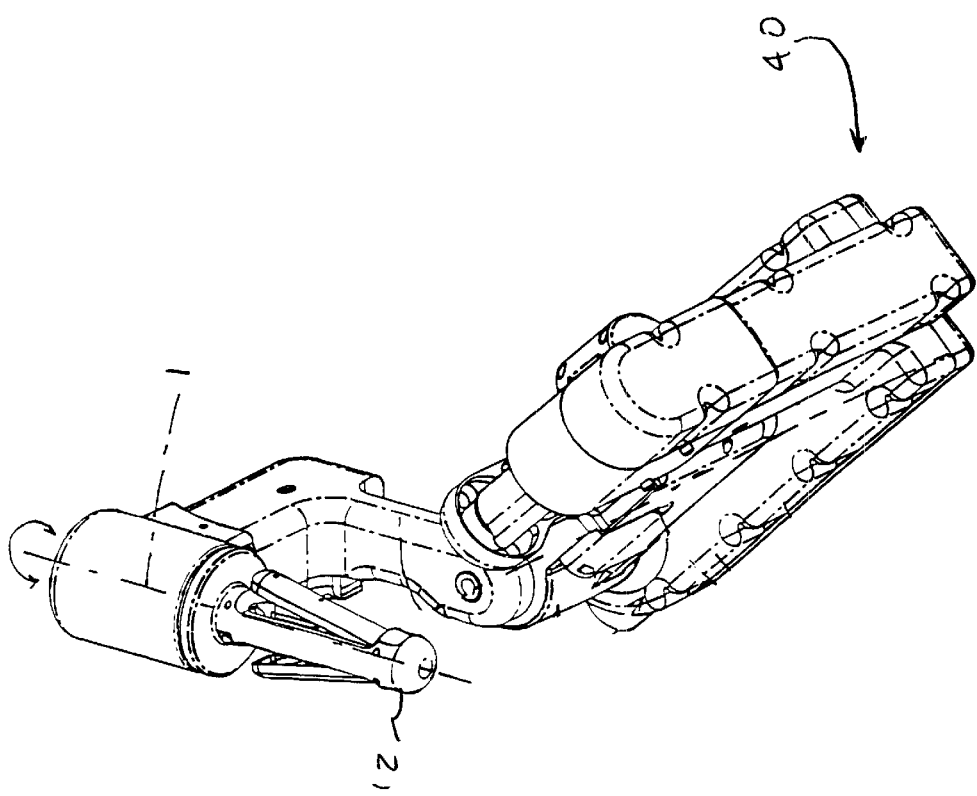

As wrist 10 includes a redundant degree of freedom, the wrist linkage may be articulated without moving the handle (and thus altering the surgeon's input). For example, referring to FIGS. 6A–C, handle 12 may be in a given orientation and location relative to platform 40 (and relative to the surrounding workspace) when the wrist linkage is located in three very different configurations. The allowable joint configurations for a given handle position mathematically define a nullspace. Nullspace motion is an internal or "self-motion" of the linkage system that yields no net motion at the output. In other words, the processor can alter the configuration of the wrist linkage within the nullspace without disturbing the handle, so long as the joint configurations remain within the nullspace during the driven joint motions.

In the exemplary embodiment, nullspace motion is simple rotation of the wrist linkage relative to platform 40 of arm 30 about joint 32. Nullspace motion for other linkage arrangements may be a vector or coordinated group of joint motions.

The nullspace at any given time is dependent on the instantaneous configuration of the wrist linkage. The processor can repeatedly calculate the wrist nullspace to determine suitable joint motions. The nullspace is preferably calculated a plurality of times each second, preferably more than about 1,000 times per second in the exemplary embodiment, 1,300 times each second or more. The processor also determines how to move the system within the nullspace so as to reduce the cost function (in the exemplary embodiment, by articulation of driven joint 32). The desired direction for actuation of the driven joint or joints may be calculated based on a calculated cost function gradient.

Figure 5B:
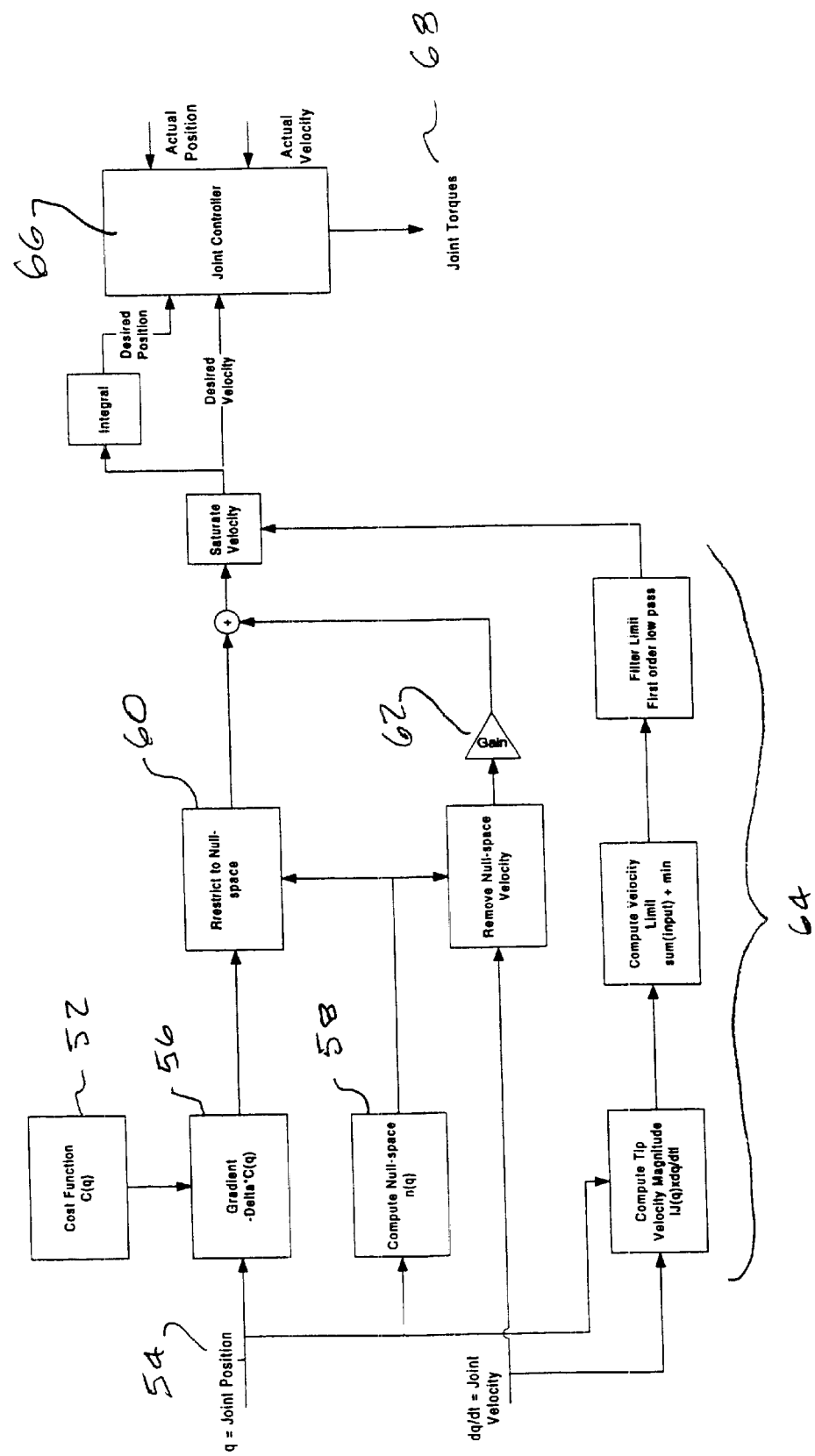

FIG. 5B depicts details of the nullspace controller 82. The cost function 52 and joint position 54 are used to determine the cost function gradient 56. This gradient may be determined using an analytical or numerical gradient. For our cost function, the cost function gradient $\nabla C(q)$ is computed as:

$$\nabla C(q)=2w_i(q_i-c_i)$$

The cost function is thus reduced for joint motions along the negative cost gradient 56. The cost function gradient is then used to derive the desired articulation of the driven joint or joints so as to reduce the cost function (and thereby avoid singularities, etc.). While the exemplary embodiment generally makes use of a single driven joint, it should be understood that a plurality of driven joints might be actively articulated by the processor.

Regardless of the calculated gradient 56, the processor will use the computed nullspace 58 to restrict motion of the driven joint or joints so that the joint configuration remains within the nullspace 60. The output of this restriction provides a set of desired joint velocities. To tailor the feel of handle 12 to the surgeon, for example, to modify or reduce friction or inertia artifacts or the like, this desired motion can be modified by nullspace velocity feedback. Hence, based on joint velocity, the nullspace velocity may be used to tailor the feel of handle 12 to the surgeon, for example, to modify or reduce friction artifacts, inertia, or the like. The joint velocity is also restricted to the nullspace, multiplied by gain 62 (typically between 0 and 1) and then added to the output of the nullspace restriction 60. Alternatively, gain 62 may be set to zero to minimize the complexity of the system.

The velocity with which the processor drives the nullspace motion by articulating the driven joint or joints may be derived based in part on the velocity with which the surgeon is moving handle 12, as can generally be understood with reference to path 64. This can provide a more natural feel, where the internal nullspace motions of the master are slow for slow or no handle movement, and fast for fast handle movement. This makes the overall internal motion behavior less noticeable and hence less disturbing.

In path 64, the processor first computes the actual handle velocity, then deduces an overall velocity limit by taking the absolute velocity magnitude and adding a small minimum velocity magnitude. Finally, the velocity limit is filtered to provide smooth operation. This filtered limit is then enforced on the desired joint velocity signals.

Using the calculated velocity limits, the processor can transmit signals indicating the desired velocity and desired position to a joint controller 66. Based on these inputs, together with the actual position and actual velocity measured by the sensor system (including the wrist potentiometers and/or encoders), the joint controller can transmit joint torques 68 to the driven joint or joints. The joint controller 66 will typically take the form of a P.D. controller, or the like.

Along with adjusting gains, it may be desired to drive one, a plurality of, or all joints of the master wrist or entire linkage. This may alter the appearance and feel to the surgeon as active motor commands and internal linkage motion may or may not be noticeable and distracting to the surgeon. It may, for example, be preferably to drive joints which are separated from handle 12, keeping the driven motor away from the hands of the surgeon so as to minimize vibration. In the preferred embodiment, only a single joint 32 is driven actively about axis 4 by controller 82, with a plurality of passive joints disposed between the driven joint and handle 12.

The exemplary embodiment also exhibits a nullspace limited to the four wrist degrees of freedom. In other words, internal motions of the linkage are confined to wrist 10. It should be understood that other embodiments may contain a large and/or complex nullspace covering some or all joints of the input linkage, which may contain more than one redundant degree of freedom.

As generally described above and/or shown in FIG. 5B, the motion about the driven joints may be adjusted by a damping term and/or a velocity limit. Both of these adjustments allow fine tuning the resulting dynamic behavior of the wrist. An instantaneous velocity limit is computed every servo cycle (1,300 times per second or more) by observing the tip velocity (how fast the surgeon is moving handle 12), adding some minimum allowable speed, and filtering the limit to achieve a desired smooth effect. The modified desired velocity is integrated into a desired position and fed to the joint controller. The joint controller compares these values against the signals from the joint sensors. Discrepancies between the desired velocity and the actual velocity result in the output torque which helps ensure system convergence toward the desired velocity and/or position, and thereby reduces the cost function. As explained above, this generally helps to keep the wrist near the center of its workspace, away from singularities, and helps keep a front side of the handle oriented toward the surgeon.

Referring now FIG. 7, third linkage 22 may optionally include a spring 60 coupled to an offset crank 62 to reduce an overturning moment which might otherwise be imposed on the surgeon's hand by handle 12. Alternatively, wrist 10 may be actively counterbalanced.

The invention provides an input device for robotic surgical techniques and other applications. The input device has a handle supported by a linkage having joints with a redundant degree of freedom, with the joints being movable with at least one more degree of freedom than the handle. At least one joint of the linkage is actively driven to prevent the linkage from approaching singularities of the joint system, motion limits of the joints, or the like, and also to drive the linkage toward a freely articulatable configuration. In one embodiment, a robotic master controller includes an arm assembly supporting a gimbal having such a redundant linkage, with the arm primarily positioning the gimbal in a three-dimensional controller workspace and the gimbal coupling the arm to the handle with four rotational degrees of freedom. One or more additional degrees of freedom may also be provided for actuation of the handle, for example, to close the jaws of a surgical grasper.

While the exemplary embodiment has been described in some detail, by way of example, an for clarity of understanding, it should be understood that a wide variety of changes, modifications, and adaptations will be obvious to those of skill in the art. Hence, the scope of the present invention is limited solely by the following claims.

What is claimed is:

1. An input device comprising:

a base;

a handle manually movable with 6 degrees of freedom relative to the base;

a linkage coupling the handle to the base, the linkage having at least 7 degrees of freedom and including at least one driven joint;

a sensor system generating input signals in response to the manual movement of the handle; and a drive system drivingly engaging the at least one driven joint so as to drive the linkage away from a motion-inhibiting configuration of the linkage during the manual movement of the handle.

2. The input device of claim 1, wherein the drive system articulates the driven joint when the handle moves the linkage toward a singularity of the linkage.

3. The input device of claim 2, wherein the linkage includes a plurality of joints, wherein the sensor system senses a configuration of the joints, and further comprising a processor coupled to the drive system, the processor directing movement of the at least one driven joint in response to the sensed configuration of the joints so as to avoid the singularity.

4. A master controller for a robotic surgical system, the master controller comprising:
   a platform;
   a handle rotatable by a hand of a surgeon about three axes relative to the platform;
   a linkage supporting the handle relative to the platform, the linkage having a joint system including at least one driven joint, the joint system defining four axes of rotation;
   a sensor system coupled to the joint system to measure motion about at least one of the joint axes of rotation;
   a drive system drivingly engaging the driven joint; and
   a processor coupling the sensor system to the drive system so that the drive system actuates the driven joint, during the rotation of the handle by the hand of the surgeon, to avoid a motion-inhibited configuration of the joint system.

5. The master controller of claim 4, wherein the processor is configured to move the driven joint away from at least one singularity of the joint system.

6. A control system for use with a master controller of a robotic surgical system, the master controller comprising a linkage coupling a handle to a platform so that the handle can be manually rotated about three orientational axes, the linkage defining four axes of rotation, and a sensor system coupled to the linkage to measure articulation about the linkage axes of rotation, the control system comprising:
   a drive system drivingly engaging a driven joint of the linkage; and
   a processor coupling the sensor system to the drive system so that the driven joint avoids a motion inhibiting configuration of the linkage during the manual rotation of the handle.

7. A method for inputting instructions into a robotic system, the method comprising:
   manually moving a handle in a controller workspace so as to articulate a linkage defining at least one singularity; and
   driving a joint of the linkage away from the at least one singularity in response to the manual movement of the handle so as to avoid inhibiting the manual movement of the handle adjacent the singularity.

8. A method for inputting commands to effect movement of a robotic arm, the method comprising:
   manually moving a handle in a controller workspace, the handle coupled to a base by a linkage so that four joints of the linkage can rotate when the handle moves;
   sensing articulation of the linkage when the handle moves;
   driving at least one of the rotational joints when the handle moves in response to the sensed articulation of the linkage so as to enhance a range of motion of the handle in the controller workspace.

9. The method of claim 8, wherein the driving step moves the linkage away from a motion-inhibiting configuration of the linkage.

10. The method of claim 9, wherein the driving step moves the linkage away from a singularity of the linkage.

11. The method of claim 8, wherein the driving step moves the linkage toward a freely-movable configuration of the linkage.

12. The method of claim 11, wherein the joints of the linkage in the freely movable configuration define a plurality of substantially orthogonal axes.

13. The method of claim 11, wherein the joints of the linkage in the freely movable configuration define substantially orthogonal yaw, pitch, and roll rotational axes of the handle.

14. The method of claim 8, wherein the handle moves with N degrees of freedom, wherein the joints define at least N+1 degrees of freedom.

15. The method of claim 14, further comprising calculating alternative linkage joint configurations for a position of the handle in the jointspace, wherein the at least one joint is driven along the calculated alternative joint configurations.

16. The method of claim 8, wherein the at least one driven joint is driven away from a handle motion inhibiting configuration caused by at least one member selected from the group consisting of a singularity of the linkage, a joint articulation limitation of the linkage, a workspace limitation, and interference with a hand grasping the handle.

17. The method of claim 8, further comprising allowing at least one of the joints to actuate passively when the handle moves.

18. The method of claim 17, wherein the at least one passive joint is disposed between the handle and the driven joint.

* * * * *